United States Patent
Kennedy

(10) Patent No.: US 7,166,281 B2
(45) Date of Patent: Jan. 23, 2007

(54) PHARMACEUTICAL COMPOSITION AND METHOD FOR RELIEVING ITCH, PAIN AND SWELLING RESULTING FROM INSECT BITES AND STINGS

(75) Inventor: Patrick Kennedy, Brenkinridge, TX (US)

(73) Assignee: American Natural Technology Sciences, Inc., Las Vegas, NV (US)

( * ) Notice: Subject to any disclaimer, the term of this patent is extended or adjusted under 35 U.S.C. 154(b) by 0 days.

(21) Appl. No.: 09/845,923

(22) Filed: Apr. 30, 2001

(65) Prior Publication Data

US 2002/0192304 A1    Dec. 19, 2002

(51) Int. Cl.
*A61K 38/46* (2006.01)
*A61K 38/43* (2006.01)
*A61K 38/54* (2006.01)

(52) U.S. Cl. .............. 424/94.65; 424/94.21; 424/94.2; 424/94.1

(58) Field of Classification Search ........ 424/725, 424/195.1, 45 B, 94.65, 94.1, 94.2, 94.21
See application file for complete search history.

(56) References Cited

U.S. PATENT DOCUMENTS

| | | | | |
|---|---|---|---|---|
| 3,383,280 | A | 5/1968 | Kuehns | 167/58 |
| 4,083,965 | A | 4/1978 | Bluhm | 424/128 |
| 4,673,526 | A | 6/1987 | Zabotto et al. | 252/174.16 |
| 5,543,149 | A | 8/1996 | Rubin | 424/405 |
| 5,716,634 | A * | 2/1998 | Tseng et al. | 424/445 |
| 5,993,857 | A | 11/1999 | Menzel et al. | 424/489 |
| 6,120,792 | A | 9/2000 | Juni | 424/448 |
| 6,325,783 | B1 | 12/2001 | Laughlin | 604/290 |
| 6,423,343 | B1 | 7/2002 | Lee et al. | 424/489 |
| 6,432,430 | B1 | 8/2002 | Fitzjarrell | 424/402 |
| 2002/0192304 | A1 | 12/2002 | Kennedy | 424/725 |

FOREIGN PATENT DOCUMENTS

| | | | |
|---|---|---|---|
| JP | 361040211 A | * | 2/1986 |
| WO | WO 00/38778 | | 12/1998 |
| WO | WO 99/37287 | * | 7/1999 |

OTHER PUBLICATIONS

Product Alert: Origins Skincare Products-Clearance Time; Never a Dull Moment, Jun. 22, 1998, full text PROMPT article, 1 page.*
Miner, K. : It's Never a Dull Moment Trying to Banish New Breakouts; Epinions.com, www.epinoins.com/content_55573778052, Feb. 9, 2002, accessed May 29, 2002.*
Greene et al. Treatment of Bee Stings; drgreen, www.drgreene.com/21_211.html, Oct. 1996, accessed May 29, 2002.*
Kerr, A. The Scent That Soothes; The Herald, Glasgow (UK): Aug. 8, 1998, p. 29 (pp. 1-2 of ProQuest).*
Smooth Operators; The Daily Telegraph, London (UK): Aug. 24, 1996, p. 043 (p. 1 of ProQuest).*

* cited by examiner

*Primary Examiner*—Patricia Leith
(74) *Attorney, Agent, or Firm*—Jack Schwartz & Associates

(57) ABSTRACT

A pharmaceutical composition for relieving the itch, pain, and swelling resulting from insect bites and stings, and methods for producing and using the composition. The method preferably comprises topically applying to the affected area the composition which contains an abrasive ingredient and an anti-itch enzyme, both of which are dispersed in a carrier containing effective amounts of emulsifiers, and/or dispersants and may take the form of a powder, liquid, or paste. The final pharmaceutical composition is preferably made in the form of a cream or lotion so that it can be rubbed directly on the skin at the affected site. The pharmaceutical composition for relieving the itch, pain, and swelling resulting from insect bites and stings disclosed herein may also contain an anesthetic and/or antibiotic.

11 Claims, No Drawings

PHARMACEUTICAL COMPOSITION AND METHOD FOR RELIEVING ITCH, PAIN AND SWELLING RESULTING FROM INSECT BITES AND STINGS

FIELD AND BACKGROUND OF THE INVENTION

The present invention relates to non-prescription topical compositions and, more specifically, to a composition including an abrasive for treating effects such as itching, pain, and swelling resulting from insect bites and stings.

DESCRIPTION OF THE PRIOR ART

There are numerous preparations presently available to provide relief from the allergenic effects of insect bites and stings. For example, U.S. Pat. Nos. 5,006,562; 4,678,668; 3,860,702; 3,825,664; 3,701,666; 3,697,287; 3,666,863; 3,515,749; 3,400,719; 3,324,002; 3,061,512; 2,917,433; 2,435,005, and 1,471,344 illustrate some such preparations. Most of these preparations are effective only to a degree and merely tend to anesthetize the site of the affected area. There is no prior art that describes a pharmaceutical composition that will draw the actual material causing the allergenic reaction from the site by way of an abrasive action, while simultaneously reducing the itch associated with insect bites and stings as in the present invention. While these units may be suitable for the particular purpose to which they address, they would not be as suitable for the purposes of the present invention as heretofore described.

SUMMARY AND OBJECTS OF THE INVENTION

The present invention relates to non-prescription topical compositions and, more specifically, to a composition including an abrasive for treating effects such as itching, pain, and swelling resulting from insect bites and stings.

It is accordingly an object of the instant invention to provide a composition for topical application for the relief of allergenic reactions caused by insect bites and stings that overcomes the shortcomings of prior art preparations.

It is a further object of the present invention to provide a composition that is able to alleviate the discomfort associated with an insect bite or sting by way of an abrasive action.

It is a yet further object of the present invention to provide a composition that is able to alleviate the discomfort associated with an insect bite or sting which is able to reduce any itching associated with the insect bite or sting.

It is a still further object of the present invention to provide a composition that is able to alleviate the discomfort associated with an insect bite or sting which is able to soothe and moisturize the affected area.

It is another object of the present invention to provide a method for producing the composition at a relatively small cost thereby making it generally available.

Another object of the present invention is to provide a composition and method for alleviating the discomfort associated with an insect bite or sting that is simple and easy to use.

A still further object of the present invention is to provide a composition that is able to alleviate the discomfort associated with an insect bite or sting that is economical in cost to manufacture.

These and other objects and advantages of the invention will become more apparent from the following detailed disclosure and claims.

Broadly speaking, the instant invention includes the provision of a topical skin preparation adapted to relieve the discomfort associated with insect bites comprising an effective amount of an abrasive ingredient (e.g. walnut shells), and an itch reducing ingredient (e.g. papain).

The present invention is directed to a method and pharmaceutical composition for reducing the itching associated with insect bites and stings. The method comprises applying a therapeutically effective amount of an abrasive ingredient and an itch reducing ingredient in a suitable pharmaceutical carrier to the surface of the skin proximate to the bite. The preferred abrasive ingredient is walnut shells and the preferred itch reducing ingredient is papain. However, any known abrasive and itch reducing ingredients may be used in the composition of the present invention. The pharmaceutical carrier may be water based.

Over the years, there have been reports of the utility of papain, commonly in the form of meat tenderizer, for the first aid treatment of hymenoptera stings. It has been suggested that a paste of the material can be applied topically and rubbed into the site of the sting, resulting in lessened swelling. The topical application of papain is effective in reducing the itch associated with insect bites.

According to the invention, a method of relieving the allergenic effects of insect stings and bites, comprises topically rubbing a pharmaceutical composition containing, among other materials, an abrasive ingredient, such as walnut shells (35–60 mesh) on the affected area.

A pharmaceutical composition for topical use in accordance with the method comprises an active abrasive ingredient, as indicated above, in a carrier suitable for topical application to the human skin, for example, in a mixture of propylene glycol and water.

The topical pharmaceutical carrier may include any substance capable of dispersing and maintaining contact between the active abrasive and anti-itch ingredients and the skin. The vehicle may be glycerin, alcohol or water based. Examples of such vehicles include aloe vera, which is a gel base, together with ethanol, isopropyl alcohol, water, and propylene glycol. Other water-based alcohol/glycerin vehicles and carriers are within the scope of the present invention.

It has been found that a pharmaceutical composition containing an abrasive ingredient works very well to alleviate the allergenic effects of insect stings and bites. Although, in the preferred embodiment disclosed herein, walnut shells (35–60 mesh), work effectively, other similarly sized abrasive materials can be used in the overall pharmaceutical composition including but not limited to any of the following: pumice, plastic materials, sand or stone, glass, seed or fruit shells, seeds, metal, any sort of brush, abrasive applicators, chitosan or ground crab shells. The remainder of the pharmaceutical composition may comprise carriers, emulsifiers, and/or dispersants and may take the form of a powder, liquid, or paste. The final pharmaceutical composition is preferably made in the form of a cream or lotion so that it can be rubbed directly on the skin at the affected site.

When the instant cream or lotion is rubbed on the bite or sting affected area, it appears that the active abrasive ingredients actually draw the allergenic or poisonous substance from the affected area along with any body materials resulting from swelling or infection.

A mild anesthetic, such as menthol, chloroform, benzocaine or an antibiotic may be added to the overall claimed abrasive pharmaceutical composition in a manner well known in the art.

A pharmaceutical composition for relieving the itch, pain, and swelling resulting from insect bites and stings, and methods for producing and using the composition is disclosed by the present invention. The method preferably comprises topically applying to the affected area the composition containing an abrasive ingredient and an anti-itch enzyme, both of which are dispersed in a carrier containing effective amounts of emulsifiers, and/or dispersants and may take the form of a powder, liquid, or paste. The final pharmaceutical composition is preferably made in the form of a cream or lotion so that it can be rubbed directly on the skin at the affected site. The pharmaceutical composition for relieving the itch, pain, and swelling resulting from insect bites and stings disclosed herein may also contain an anesthetic and/or antibiotic.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

DETAILED DESCRIPTION OF A PREFERRED EMBODIMENT

It has been found that very effective relief from the allergenic effects of insect bites and stings may be had by topically applying to the affected area a pharmaceutical composition containing an abrasive ingredient such as walnut shells. While satisfactory relief is obtained by applying a pharmaceutical composition containing 35–60 mesh walnut shells as an abrasive ingredient, the addition of polysorbate 60 and an itch-reducing enzyme papain to the overall pharmaceutical composition result in effective relief within a shorter time period from when the composition is rubbed on the area affected by the insect bite or sting. In place of papain, the itch-reducing enzyme may be an ingredient selected from the group of subtilisin or pancreatin. Not only is the itching relieved by way of the enzyme papain, subtilisin or pancreatin, but any attendant swelling that has occurred is also removed by way of the abrasive action of the walnut shells, and further swelling, itching or other allergenic effects are thus prevented.

The preferred embodiment of the herein disclosed pharmaceutical composition contains the ingredients comprising polysorbate 60 and papain, together with the abrasive ingredient. The abrasive ingredient is preferably meshed walnut shells. However, any abrasive material may be substituted therefore. It is believed that these ingredients operate effectively to draw the acids, mucoids, poisons, and similar debris from the site of the sting or bite. These acids, mucoids, poisons, and debris are then absorbed, neutralized and diluted in the composition while being simultaneously rubbed off from the affected body site.

In addition to the above listed ingredients, it is preferred that the pharmaceutical composition also contains isopropyl palmitate and pentaerythrityl tetracapryate/caprate or other detersives as carriers and cleaning agents and to improve skin adhesion when in a wet state; catrearyl alcohol, propylene glycol, ethyl alcohol or other polyhydric alcohols to avoid drying; binders and emulsifiers such as poliwax emulsifying wax NF; the water soluble salts of cellulose ethers such as NaHCO₃; and finally, water as a solvent.

Other inert ingredients that may be used in this invention include: vegetable and fruit oils, soaps, surfactants, lubricants, mineral oils, petrolatum, gels, lotions, emollients, white petroleum, beeswax, di-propylene glycol, gums, lubricating jelly and olive oils. Other active ingredients that may be used in this invention include: menthol, antihistamines sold under the trademark BENADRYL®, diphenhydramine hydrochloride, germicidal disinfectants, aloe/aloe vera, silicone, antiseptic preparations, antimicrobial agents such as PCMX, broad spectrum surface disinfectants, lidocaine, boric acid/borates, vitamins, oils from flowers, plants or animals, antibiotic ointments sold under the trademark NEOSPORIN®, hydrocortisone cream/acetate, swelling and pain reducers, benzocaine, isobutene, hydrogen peroxide, iodine, zinc acetate, ammonia hydroxide, citronella, peppermint oil, analgesic/antihistamine ingredients, calamine, camphor, clove oil and methylparaben. It is preferred that the pharmaceutical composition be in the form of a cream or lotion for easy application and adhesion to the affected area, although a pharmaceutical composition in other forms, such as powder, could be used. If stored in powdered form, a small amount of water can be mixed with the powdered composition before use to improve the adhesive and abrasive qualities of the pharmaceutical composition.

The maximum concentration of the active ingredient is limited only by the desired form and consistency of the pharmaceutical composition. Active ingredient concentrations over those listed in the preferred embodiment may be used while still obtaining a satisfactory cream consistency. The preferred concentration of the active ingredients from the standpoint of fast action, abrasive capacity, and cosmetic quality of the pharmaceutical composition as a cream, is between 20% and 60%. At low concentrations of the active ingredient the composition acts more slowly and has smaller abrasive capacity. The pharmaceutical composition appears to work well down to about 20% or less active ingredient concentration particularly for small bites or stings.

A preferred example of a formulation for the pharmaceutical composition disclosed herein, given in weight percentages, is:

| | |
|---|---|
| Walnut Shells (30–60 mesh) | 15.00% |
| Papain | 00.10% |
| Polysorbate 60 | 03.00% |
| Isopropyl Palmitate | 03.50% |
| Pentaerythrityl Tetracapryate/caprate | 03.50% |
| Poliwax emulsifying wax NF | 04.00% |
| Cetrearyl alcohol | 03.00% |
| Ethyl alcohol | 00.10% |
| Sodium Hydroxide | qs pH = 8.50 |
| NaHCO₃ | 02.00% |
| Propylene Glycol | 04.00% |
| Water (distilled) | 61.08% |

A range of weight percentages for the formulation of the pharmaceutical composition disclosed herein is as follows:

| | |
|---|---|
| Walnut Shells (30–60 mesh) | 5.00–25.00% |
| Papain | .01–1.00% |
| Polysorbate 60 | 1.00–6.00% |
| Isopropyl Palmitate | 1.00–6.00% |
| Pentaerythrityl Tetracapryate/caprate | 1.00–6.00% |
| Poliwax emulsifying wax NE | 2.00–8.00% |
| Cetrearyl alcohol | 2.00–7.00% |
| Ethyl alcohol | 0.10–5.00% |
| Sodium Hydroxide | qs pH = 8.50 |
| NaHCO₃ | 0.50–5.00% |
| Propylene Glycol | 1.00–6.00% |
| Water (distilled) | remainder of composition |

All of the ingredients are preferably in the form of powder before mixing except glycerine and water.

The abrasive anti-sting pharmaceutical composition of the present invention using the above listed ingredients is prepared according to the following steps:

1) Add the water and the propylene glycol to a first vessel and heat to 75 degrees Celsius with stirring;

2) Add to a second vessel the Polysorbate 60, Isopropyl Palmitate, Pentaerythrityl Tetracapryate/caprate, Poliwax emulsifying wax NF, Cetrearyl alcohol, and heat to 75 degrees Celsius with some stirring until homogeneous;

3) With rapid mixing, add the contents of the second vessel slowly to the first vessel and add Ethyl alcohol;

4) Remove the combined mixture in vessel 1 from the heat and start cooling;

5) At 50 degrees Celsius stir in the meshed walnut shells, NaCHO3 and the papain;

6) Adjust the PH to 7.50 and stir in the Sodium Hydroxide;

7) Check the pH again and adjust if necessary.

The pharmaceutical composition having an abrasive action is now ready for application to the affected site for treating insect bites and stings.

In actual use to treat insect stings and bites, when the pharmaceutical composition is applied to the site soon after the sting or bite occurs, effective relief is had in a matter of seconds. In instances of severe allergenic effects or reactions to insect bites and stings, it is important to apply the pharmaceutical composition immediately after the sting or bite is received so that the allergenic material can be withdrawn rapidly from the body before getting into the bloodstream.

Whereas the invention has been described herein with reference to the presently preferred pharmaceutical composition listed above, it should be understood that various changes may be made by one skilled in the art without departing from the disclosed inventive concepts particularly pointed out above and as claimed by me hereinafter.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

I claim:

1. A pharmaceutical composition for topical application to a site of insect bites and stings to relieve any of itch, pain, and swelling associated therewith, consisting of an effective amount of an abrasive ingredient and a carrier, wherein upon application by a user said composition is able to relieve any of the itch, pain and swelling caused by the insect bites and stings at said site;
   wherein said abrasive ingredient is selected from the group consisting of walnut shell, pumice, plastic material, sand, stone, seed shell, fruit shell, seed, metal, chitosan and ground crab shell;
   wherein said carrier is selected from the group consisting of vegetable oil, fruit oil, soap, surfactant, lubricant, mineral oil, petrolatum, gel, lotion, emollient, white petroleum, beeswax, di-propylene glycol, gum, lubricating jelly and olive oil; and an itch-reducing amount of an enzyme chosen from the group consisting of papain, subtilisin, and pancreatin, wherein said pharmaceutical composition is applied to a surface of skin proximate to said insect bite or sting.

2. The pharmaceutical composition for topical application according to claim 1, wherein the composition is in the form of a lotion.

3. The pharmaceutical composition for topical application according to claim 1, wherein the composition is in the form of a paste.

4. The pharmaceutical composition for topical application according to claim 1, wherein the composition is in the form of a liquid.

5. The pharmaceutical composition according to claim 1 wherein said abrasive ingredient and said anti-itch enzyme are applied as a solution in an aqueous pharmaceutical carrier.

6. The pharmaceutical composition for topical application according to claim 1, further comprising an active ingredient.

7. The pharmaceutical composition for topical application as recited in claim 6, wherein the active ingredient is selected from the group consisting of menthol, antihistamines, diphenhydramine hydrochloride, germicidal disinfectant, aloe, aloe vera, silicone, antiseptic preparations, antimicrobial agents, triclosan, broad spectrum surface disinfectants, lidocaine, boric acid, borates, vitamins, oils from flowers, oils from plants, oils from animals, antibiotic ointments, hydrocortisone cream, hydrocortisone acetate, swelling and pain reducers, benzocaine, isobutene, hydrogen peroxide, iodine, zinc acetate, ammonia hydroxide, citronella, peppermint oil, analgesic ingredients, antihistamine ingredients, calamine, camphor, clove oil, a composition having the chemical formula NaCHO3 and methylparaben.

8. A pharmaceutical composition for topical application to a site of insect bites and stings to relieve any of itch, pain, and swelling associated therewith, consisting of effective amount of an abrasive ingredient, an itch-reducing enzyme selected from at least one of papain, subtilisin, and pancreatin and a carrier for said abrasive ingredient and said itch-reducing enzyme suitable for topical application to the site of the insect bite or sting, wherein upon application by a user said composition is able to relieve any of the itch, pain and swelling caused by the insect bites and stings at said site;
   wherein said abrasive ingredient is selected from the group consisting of walnut shell, pumice, plastic material, sand, stone, seed shell, fruit shell, seed, metal, chitosan and ground crab shell;
   wherein said carrier is selected from the group consisting of vegetable oil, fruit oil, soap, surfactant, lubricant, mineral oil, petrolatum, gel, lotion, emollient, white petroleum, beeswax, di-propylene glycol, gum, lubricating jelly and olive oil.

9. The pharmaceutical composition for topical application according to claim 8, wherein the composition is in the form of a lotion.

10. The pharmaceutical composition for topical application according to claim 8, wherein the composition is in the form of a paste.

11. The pharmaceutical composition for topical application according to claim 8, wherein the composition is in the form of a liquid.

* * * * *